(12) United States Patent
Harris et al.

(10) Patent No.: US 7,699,829 B2
(45) Date of Patent: Apr. 20, 2010

(54) CATHETER WITH SENSOR TIP AND METHOD OF USE OF SAME

(75) Inventors: Chad G. Harris, Albertsville, MN (US); Matthew L. Hawk, Otsego, MN (US); Timothy J. Mickley, Elk River, MN (US); Dorin Panescu, San Jose, CA (US); Maria Palasis, Wellesley, MA (US); Jacob Rooney, Belgrade, MN (US); Toby Freyman, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 136 days.

(21) Appl. No.: 11/037,154

(22) Filed: Jan. 19, 2005

(65) Prior Publication Data
US 2006/0030833 A1 Feb. 9, 2006

Related U.S. Application Data

(60) Provisional application No. 60/556,059, filed on Mar. 25, 2004.

(51) Int. Cl.
*A61M 31/00* (2006.01)
(52) U.S. Cl. .................. 604/503; 604/264; 604/508
(58) Field of Classification Search .................. 604/503, 604/264; 607/122
See application file for complete search history.

(56) References Cited

U.S. PATENT DOCUMENTS

| | | | |
|---|---|---|---|
| 4,282,886 A | * 8/1981 | King | .................. 607/130 |
| 4,936,281 A | * 6/1990 | Stasz | .................. 600/439 |
| RE33,925 E | * 5/1992 | Bales et al. | .................. 606/48 |
| 5,403,311 A | 4/1995 | Abele et al. | |
| 5,807,324 A | * 9/1998 | Griffin, III | .................. 604/529 |
| 6,102,887 A | * 8/2000 | Altman | .................. 604/22 |
| 6,212,434 B1 | * 4/2001 | Scheiner et al. | .................. 607/123 |
| 2003/0105436 A1 | * 6/2003 | Ponzi | .................. 604/264 |
| 2003/0135166 A1 | * 7/2003 | Gonnelli | .................. 604/264 |
| 2004/0220471 A1 | * 11/2004 | Schwartz | .................. 600/424 |

FOREIGN PATENT DOCUMENTS

| | | | |
|---|---|---|---|
| FR | 2 365 351 A | | 4/1978 |
| FR | 2365351 A | * | 5/1978 |
| WO | WO 02/11808 A | | 2/2002 |
| WO | WO 02/071955 A | | 9/2002 |
| WO | WO 03/095016 A | | 11/2003 |

* cited by examiner

*Primary Examiner*—Nicholas D Lucchesi
*Assistant Examiner*—Laura A Bouchelle
(74) *Attorney, Agent, or Firm*—Vidas, Arrett & Steinkraus P.A.

(57) ABSTRACT

An apparatus and method for catheter-based sensing and injection at a target site within a patient's body. An injection catheter is equipped with electrodes at its distal end which contact the surface of a target site, such as an AV node of the heart. Electrical signals detected at the target site by the electrodes are fed via leads to the proximal end of the catheter, where they are received by a monitor, such as an EKG monitor. If the electrical signals satisfy predetermined criteria, a needle within the catheter is extended into the target site, and a therapeutic agent is injected into the target site.

40 Claims, 6 Drawing Sheets

CATHETER WITH SENSOR TIP AND METHOD OF USE OF SAME

CROSS REFERENCE TO RELATED PATENT APPLICATION

The present application claims the benefit of priority of U.S. Provisional Patent Application No. 60/556,059, filed Mar. 25, 2004.

FIELD OF THE INVENTION

Embodiments of the present invention relate to catheter-based sensors and methods for the injection of therapeutic and other agents at a target site within a patient's body. More particularly, the embodiments relate to catheter-based injection systems with electric sensors.

BACKGROUND

Medical catheters are used for innumerable minimally invasive medical procedures. Catheters may be used, for example, for delivery of therapeutic drug doses to target tissue and/or for delivery of medical devices such as lumen-reinforcing or drug-eluting stents. Likewise, catheters may be used to guide medical instruments to a target site to perform a surgical procedure, such as tissue rescission, ablation of obstructive deposits or myocardial revascularization.

Currently, catheter-based systems that are equipped with sensors (for example, electrodes) have a sensor tip at the distal end of the catheter. The sensor tip may or may not have an opening to permit a needle or a medical device to pass through the opening and into target tissue in the patient. These systems usually have one or more additional return sensors implemented as bands circumferentially around the catheter. In some systems, tissue contact is determined by measuring the impedance between the tip sensor when it is in contact with tissue and a return sensor that is not in contact with the tissue but is only in contact with a fluid, for example, blood, that is surrounding the tissue. However, this determination is based on known, that is, pre-determined, impedance values when the electrode is in contact with tissue and when only in contact with body fluids (for example, blood). Unfortunately, this method is not without problems, since the impedances of tissue and body fluid (for example, blood) are known to change during a procedure and different tissue will have different impedances depending on whether the tissue is healthy or diseased.

Alternatively, other sensor systems using a tip sensor and one or more band sensors around the catheter determine tissue contact by measuring impedance between sensors when the sensors are both contacting the tissue. Consequently, for this type of catheter to be able to detect the impedance, it must be lying flat against the target tissue area so that at least two of the sensors are in contact with the tissue. Unfortunately, this position does not enable the optimal targeted delivery of therapeutic agents to provide the most effective treatment regimen, since the tissue determined to be the target is usually not directly in line with the tip of the catheter.

SUMMARY OF THE INVENTION

The invention is directed to improved catheter systems with sensors and related methods. In certain embodiments, a device and method are provided for injecting therapeutic and other fluids at a target site within a patient's body. The device may include a catheter with a distal end and a proximal end, at least one lumen extending therebetween, at least one needle extending the length of the lumen, and a sensor located at the distal end of the catheter to detect characteristic electrical signals. The sensor may have at least one opening co-axially aligned with the lumen to permit the at least one needle to extend through the opening and out of the catheter. The device may also include at least two sensor leads, a distal end of each of the sensor leads in electrical communication with the sensor, and a proximal end of each of the sensor leads extending to the catheter proximal end where they may be connected to a monitoring device, for example, an electrocardiogram (EKG).

Other aspects of the invention are set forth in the appended claims.

BRIEF DESCRIPTION OF THE DRAWINGS

The foregoing and further features and advantages of the invention will become apparent from the following description of preferred embodiments with reference to the accompanying drawings, wherein like numerals are used to represent like elements and wherein.

DETAILED DESCRIPTION

Some embodiments of the present invention may include a needle-based direct injection device similar to, for example, a Stiletto catheter manufactured by Boston Scientific of Natick, Mass., with an electrode sensor tip. In some embodiments, the sensor tip may include at least two electrodes separated by an insulator and connected to a monitoring device, for example, an electrocardiogram (EKG) to permit the monitoring of electrical signals in tissue that is in contact with the electrodes. For example, if the sensor tip were placed at a specific location (e.g., the pulmonary veins, left ventricle and AV node of the heart), the sensor tip may read any distinct electrical patterns generated by the tissue. Therefore, the sensor tip may be used to locate a characteristic electrical pattern known to be associated with a specific tissue location and target the location for the injection of therapeutics.

It is believed that injecting certain therapeutic agents, for example, certain genetic substances, into the pulmonary veins, left ventricle and AV node of the heart may provide a superior treatment for certain arrhythmias, such as, bradyarrhythmia and ventricular tachyarrhythmia. Unfortunately, current treatments, for example, oral drugs, radio frequency ablation, and implantable devices lack the desired effectiveness and have undesirable side effects. Fortunately, direct injection of a therapeutic agent, for example, a gene therapy agent, into the target tissue may provide a significantly improved effectiveness and with fewer side effects.

Figure 1:
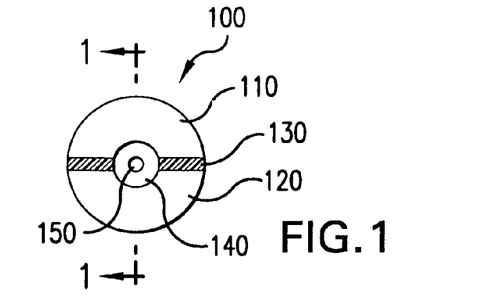
FIG. 1 is a front-end view of a distal end of a catheter with sensing electrodes, in accordance with an embodiment of the present invention.

FIG. 1 is a front-end view of a distal end of a catheter with sensing electrodes, in accordance with an embodiment of the present invention. In FIG. 1, a sensor 100 may include a first electrode 110 and a second electrode 120 with an insulator 130 between them to form a generally circular disk shape that may be affixed directly to a distal end of the catheter. Electrodes 110, 120 may be made of any electrically conductive material, for example, #304 stainless steel or like conductive, surgical material and may be of sufficient thickness to prevent deformation of sensor 100 when it contacts tissue. Sensor 100 may have a smooth, a rough and/or a slightly adhesive surface on its distal end. The rough and slightly adhesive surfaces may help prevent sensor 100 from "jumping" off the tissue when the needle is deployed.

In an alternate embodiment, sensor 100 may have small protrusions on its distal end that may penetrate or merely depress tissue when placed against the tissue to also help prevent sensor 100 from "jumping" off the tissue when the needle is deployed. Each of the jumping prevention embodiments may be particularly useful in locations that may experience significant movement of the tissue, for example, an AV node of the heart.

In FIG. 1, insulator 130 may include any non-conductive material or adhesive, for example, a urethane adhesive, having, but not limited to, a thickness of approximately 0.020 or more inches between electrodes 110, 120. For example, in addition to greater thickness, for example, 0.030 and 0.040 inches, insulator 130 may be of a thickness of less than 0.020 inches depending on the propensity of first electrode 110 and second electrode 120 to short circuit each other. Insulator 130 may also include TEFLON™ or a non-conductive plastic. Sensor 100 may also have an axially disposed opening 140 extending from its proximal surface to its distal surface for communication with and axially aligned with a lumen in the catheter. Opening 140 may be of sufficient diameter to permit the extension and retraction of a needle 150 through sensor 100 without contacting needle 150 against either first electrode 110 or second electrode 120. In accordance with embodiments of the present invention, sensor 100 may be manufactured and the sizing of opening 140 may be set by inserting a non-stick core, for example, TEFLON™, between first electrode 110 and second electrode 120 and sliding the two electrodes and non-stick core into a non-stick tube, for example, a TEFLON™ tube, having a predetermined internal diameter. Wicking and/or injecting the adhesive into the gap between electrodes 110, 120 may insert an adhesive, for example, an insulating adhesive. When the adhesive has set, sensor 100 may be removed from the non-stick tube, the non-stick core may be removed from opening 140, and any excess adhesive may be trimmed from sensor 100. Alternatively, first electrode 110 and second electrode 120 may have an adhesive applied to their respective opposing side faces and the non-stick core and one or more preformed insulating pieces may be assembled between first electrode 110 and second electrode 120 and then the entire assembly may be slid into the non-stick tube, or some other clamping device until the adhesive may set. Still further, other manufacturing techniques, including injection molding, may be used as well.

In FIG. 1, although the shape of sensor 100 may be shown in this embodiment as being generally circular, the shape is not determinative of how sensor 100 operates, and other embodiments are possible, for example, oval/ovoid, square and hemispherical shapes, some of which will be shown and detailed in subsequent figures and description. Insulator 130, for example, may be used to fix the electrodes 110, 120 together. Likewise, other embodiments are contemplated in which sensor 100 may be segmented into three or more electrodes that may be fixed to, but electrically insulated from, each other. Likewise, in accordance with an embodiment of the present invention, insulator 130 may extend around the inside of opening 140 to form an annular insulating band, which may further assure that needle 150 does not touch either first electrode 110 or second electrode 120. Alternatively, a separate insulator, an insulated needle and/or a non-conductive needle may be used for this purpose. Similarly, in accordance with an embodiment of the present invention, sensor 100 may be a single electrode with two or more spatially oriented lead wires attached thereto to act as a thermocouple detection device by measuring the impedance between the lead wires.

Figure 2:
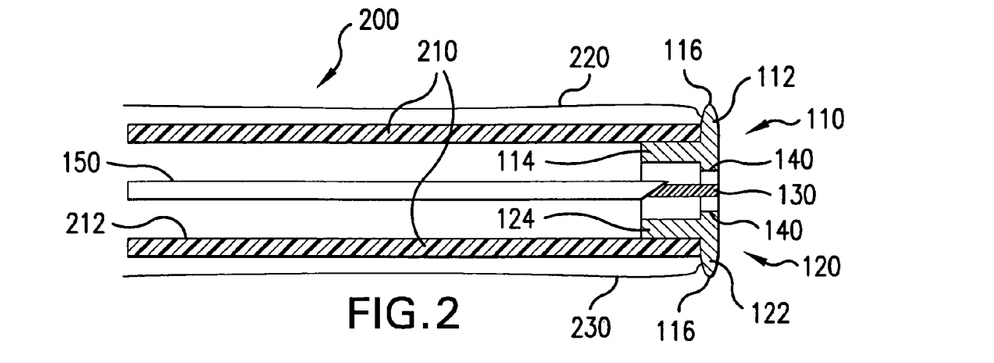
FIG. 2 is a cross-sectional side view of the distal end of the catheter of FIG. 1 along line 1-1, in accordance with an embodiment of the present invention.

FIG. 2 is a cross-sectional side view of the distal end of the catheter of FIG. 1 along line 1-1, in accordance with an embodiment of the present invention. In FIG. 2, first electrode 110 may include an end plate 112 and a generally semicircular, cylindrical wall 114 generally perpendicular to and extending proximally from a proximal side of end plate 112. End plate 112 may have an outer circular edge 116 that may be rounded to present a smooth, sliding surface for easy extension and retraction of the catheter from a patient. Likewise, second electrode 120 may include an end plate 122 and a generally semicircular, cylindrical wall 124 generally perpendicular to and extending proximally from a proximal side of end plate 122. Generally, semicircular, cylindrical wall portions 114, 124 may be separated from, and possibly affixed to, each other by a portion of insulator 130, which may extend proximally from the proximal sides of end plates 112, 122.

In FIG. 2, in accordance with an embodiment of the present invention, a sensor tip injection device 200 may include sensor 100, which, for example, may be affixed to the interior diameter of the distal end of a catheter 210, with catheter 210 having a lumen extending from a proximal end to the distal end. Alternatively, sensor 100 may be affixed to the exterior diameter of the distal end of catheter 210. Sensor 100 may be affixed to the distal end of catheter 210 with the same and/or different adhesive used to form insulator 130 (in those embodiments where insulator 130 is formed of adhesive), which may help to further insulate sensor 100 from the remainder of sensor tip injection device 200. Specifically, exterior sides of cylindrical walls 114, 124 of sensor 100 may be affixed to a catheter interior wall 212, which may define the lumen. A first lead wire 220 may extend from the proximal end of catheter 210 along the exterior wall of catheter 210 to the distal end of catheter 210 to be electrically coupled with first electrode 110. For example, first lead wire 220 may attach to the proximal side of end plate 112 of first electrode 110. Similarly, a second lead wire 230 may be similarly arranged and connected to a proximal side of end plate 122. First lead wire 220 and second lead wire 230 may each be attached to the exterior of catheter 210 along its length, at selected points, or not at all. In an embodiment of the present invention, lead wires 220, 230 may be of approximately 36-gauge wire, which may include copper and/or copper-clad stainless steel wire. Likewise, the wire may have a Polyimide insulation coating. In an embodiment of the present invention, a protective outer covering/sheathing (not shown) may enclose first lead wire 220 and second lead wire 230. The protective outer covering/sheathing may be, for example, a resin, a plastic and/or a heat shrink-wrap. The proximal ends of each of first lead wire 220 and second lead wire 230 may be connected to monitoring equipment, for example, an EKG monitor and/or a thermocouple monitor, to measure the electrical signals in the target tissue, for example, electrical signals indicative of bradyarrhythmia and/or ventricular tachyarrhythmia at the AV node of the heart.

In FIG. 2, although this embodiment shows a single needle sensor tip injection device with generally planar distal sides of end plates 112, 122, various other embodiments are contemplated which may include, for example, multiple needles and/or rounded sensors 100, which may have a slightly dome-like shape.

In FIG. 2, in accordance with an embodiment of the present invention, sensor tip injection device 200 may be used to identify a specific tissue location within a patient to deliver a therapeutic. For example, sensor tip injection device 200 may be located on the specific tissue location by moving sensor 100 until it detects a known/predetermined characteristic electrical signal for the desired specific tissue location thereby signifying contact. At this point, needle 150 may be actuated to extend through opening 140 in sensor 100 to enter the specific tissue location to deliver the therapeutic in exactly the desired location. Alternate embodiments of needle 150 are also contemplated to overcome the potential loss of therapeutic at the injection site. For example, needle 150 may have a helical or a corkscrew-like shape that may be inserted into the specific tissue location to produce a deeper/longer needle hole, which may result in more of the therapeutic being retained in the tissue. In yet another embodiment to minimize the loss of therapeutic at the injection site, needled 150 may include a solid therapeutic, for example, a polymer and cells, that may break-off in predetermined lengths when the needle is extended beyond the distal end of catheter 210 and into the target tissue.

Figure 3:
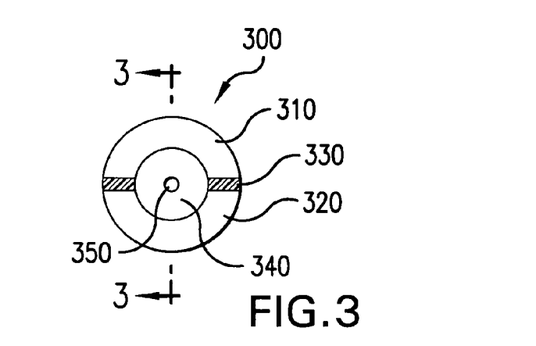
FIG. 3 is a front-end view of a distal end of a catheter with sensing electrodes, in accordance with another embodiment of the present invention.

FIG. 3 is a front-end view of a distal end of another embodiment of the catheter in FIG. 1. In FIG. 3, a sensor 300 may include a first electrode 310 and a second electrode 320 that may be separated from, and possibly fixed to, each other by an insulator 330, to form a generally circular disk shape that may be affixed directly to a distal end of the catheter. As with sensor 100 in FIG. 1, in FIG. 3, electrodes 310, 320 may be made of any electrically conductive material, for example, # 304 stainless steel or like conductive, surgical material, and may be of sufficient thickness to prevent deformation of sensor 300 when it contacts tissue. Insulator 330 also may include any non-conductive adhesive, for example, a urethane adhesive, having, but not limited to, a thickness of approximately 0.020 or more inches between electrodes 310, 320.

For example, insulator 330 may be of similar manufacture as described above in relation to sensor 100. Again, similar to sensor 100 in FIG. 1, in FIG. 3, sensor 300 may have an axially disposed opening 340 extending from its proximal surface to its distal surface for communication with and axially aligned with a lumen in the catheter. In sensor 300, opening 340 is shown as being larger than opening 140 in sensor 100. In another embodiment of the present invention, opening 340 in sensor 300 may be smaller than opening 140 in sensor 100. Regardless, opening 340 may be of sufficient diameter to permit the extension and retraction of at least one needle 350 through sensor 300 without contacting either first electrode 310 or second electrode 320.

In FIG. 3, although the shape of sensor 300 may be shown in this embodiment as being generally circular, the shape is not determinative of how sensor 300 may operate, and other embodiments are possible, for example, oval/ovoid, square and hemispherical shapes, some of which will be shown and detailed in subsequent figures and description. As with sensor 100, other embodiments are contemplated in which sensor 300 may be segmented into three or more electrodes that may be fixed to, but electrically insulated from, each other by insulator 330. Likewise, in accordance with an embodiment of the present invention, insulator 330 may extend around the inside of opening 340 to form an annular insulating band (not shown), which may further assure that needle 350 does not touch either first electrode 310 or second electrode 320 and cause a short in the signal from either electrode. Alternatively, a separate insulator may be used for this purpose. Similarly, in accordance with an embodiment of the present invention, sensor 300 may be a single electrode with two or more spatially oriented lead wires attached thereto to act as a thermocouple detection device by measuring the impedance between the lead wires.

Figure 4:
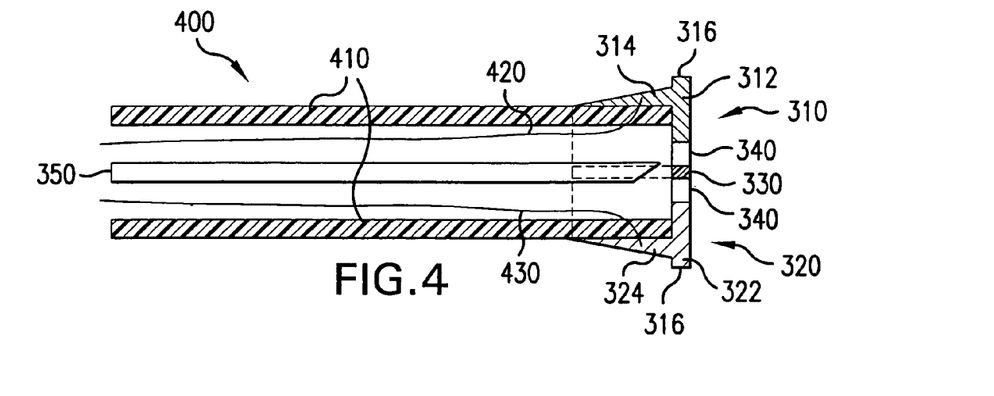
FIG. 4 is a cross-sectional side view of the distal end of the catheter of FIG. 3 along line 3-3, in accordance with an embodiment of the present invention.

FIG. 4 is a cross-sectional side view of the distal end of the catheter of FIG. 3 along line 3-3, in accordance with an embodiment of the present invention. In FIG. 4, a sensor tip injection device 400 may include first electrode 310 and second electrode 320, which may each include an end plate 312, 322 and a tapered, generally semicircular, cylindrical wall 314, 324 generally perpendicular to and extending proximally from a proximal side of each end plate 312, 322, respectively. End plates 312, 322 may have an outer circular edge 316 that may be generally square in cross-sectional profile in order to provide a substantially planar contacting surface of end plates 312, 322. Other embodiments are contemplated in which, for example, outer circular edge 316 also may be rounded as in sensor 100, or only slightly rounded over at the corners of circular edge 316, or rounded over from the distal side of end plates 312, 322 to the proximal side of end plates 312, 322, etc. Generally semicircular, cylindrical wall portions 314, 324 may be separated from, and possibly affixed to, each other by a portion of insulator 330 (shown as hidden lines), which may extend proximally from end plates 312, 322. An exterior edge of each of generally semicircular, cylindrical wall portions 314, 324 may each be tapered away from their respective end plates 312, 322 toward the exterior side wall of catheter 410 to form a wedge-like shape.

In FIG. 4, sensor tip injection device 400 may include sensor 300, which may be affixed to an outside diameter of the distal end of a catheter 410, with catheter 410 having a lumen extending from a proximal end to the distal end of catheter 410. Alternatively, sensor 300 may be affixed to the interior diameter of the distal end of catheter 410. In such an embodiment, the tapering of semicircular, cylindrical wall portions 314, 324 may be reversed to taper away from the central axis of opening 340 to the interior wall of catheter 410. Such a configuration may aid in guiding and centering needle 350 when it is extended through opening 340. Sensor 300 may be affixed to the distal end of catheter 410 with the same and/or different adhesive used to form insulator 330 (in cases where insulator 330 is formed of adhesive), which may help to further insulate sensor 300 from the remainder of sensor tip injection device 400. Specifically, interior sides of cylindrical walls 314, 324 of sensor 300 may be affixed to an exterior wall of catheter 410. The opposite, interior wall of catheter 410 may define the lumen that extends from the proximal end to the distal end of catheter 410.

In FIG. 4, a first lead wire 420 and a second lead wire 430 may extend from the proximal end of catheter 410 along the interior wall of catheter 410 and through the interior wall of the distal end to be electrically coupled with first electrode 310 and second electrode 320, respectively. For example, first lead wire 420 may couple to cylindrical wall 314 of end plate 312, and second lead wire 430 may attach to cylindrical wall 324 of end plate 322. First lead wire 420 and second lead wire 430 may each be attached to the interior lumen walls of catheter 410 along its length, at selected points, or not at all. In another embodiment of the present invention, first lead wire 420 may be coupled to the proximal side of first electrode end plate 312 that may overhang the distal end of catheter 410, and second lead wire 430 may be coupled to the proximal side of second electrode end plate 322 that may overhang the distal end of catheter 410. In embodiments of the present invention, each lead wire 420, 430 may be directly coupled to their respective electrodes 310, 320 through the interior of catheter 410 or by passing through the interior lumen walls at the distal end of catheter 410 and then into electrodes 310, 320, respectively.

In FIG. 4, like FIG. 1, the embodiment shows only a single needle sensor tip injection device with generally planar distal sides of sensor end plates 312, 322, but various other embodiments are contemplated which may include, for example, multiple needles and/or rounded sensors 300, which may include end plates having a slightly dome-like shape.

Similar to sensor tip injection device 200, in accordance with an embodiment of the present invention, in FIG. 4, sensor tip injection device 400 may be used to identify a specific tissue location within a patient to deliver a therapeutic. For example, sensor tip injection device 400 may be located over the specific tissue location by moving sensor 300 until the distal sides of end plates 312, 322 detect a known/predetermined characteristic electrical signal for the desired specific tissue location, thereby signifying contact. At this point, needle 350 may be actuated to extend through opening 340 in sensor 300 to enter the specific tissue location to deliver the therapeutic in exactly the desired location. As in FIG. 2, alternate embodiments of needle 350 are also contemplated to overcome the potential loss of therapeutic at the injection site. For example, needle 350 may have a helical and/or a corkscrew-like shape that may be inserted into the specific tissue location to produce a deeper/longer needle hole, which may hold more of the therapeutic in the tissue.

Figure 5:
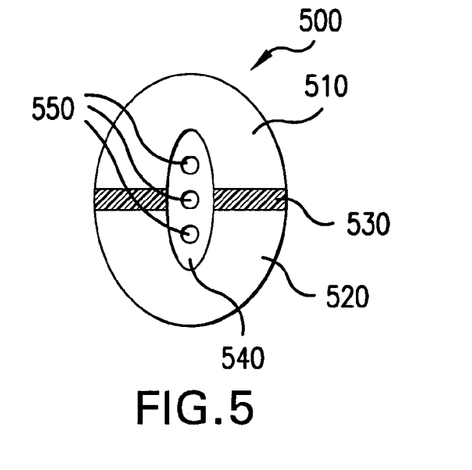
FIG. 5 is a front-end view of a distal end of a catheter with sensing electrodes, in accordance with yet another embodiment of the present invention.

FIG. 5 is a front-end view of a distal end of a catheter with sensing electrodes, in accordance with another embodiment of the present invention. In FIG. 5, a sensor 500 may include a first electrode 510 and a second electrode 520 with an insulator 530 between them to form a generally oval shape. In addition, an opening 540 may be located in sensor 500 and may be of a generally oval shape to permit one or more needles 550 to be introduced through opening 540. For example, in the embodiment of the present invention shown in FIG. 5, opening 540 may be substantially axially aligned with the center of sensor 500 and may accommodate multiple, for example, three, needles 550. However, alternative embodiments are contemplated in which less than three as well as more than three needles may be used. Regardless of the number of needles, in accordance with embodiments of the present invention, this and all multiple lumen, for example, needle and/or needle-less, designs may be used to polymerize two or more therapeutic agents upon injection. This may be accomplished by keeping each of the therapeutic agents from mixing until they are injected and/or delivered to the tissue. In the needle-less embodiments, the therapeutic may be delivered to but not injected into the target tissue.

In FIG. 5, although not shown, sensor 500 may also have perpendicular and proximally extending walls similar to cylindrical walls 114, 124 in FIG. 2 and cylindrical walls 314, 324 in FIG. 4 to fit into or over the distal end of a catheter. Alternative shapes are contemplated including, for example, oval and/or square.

Figure 6:
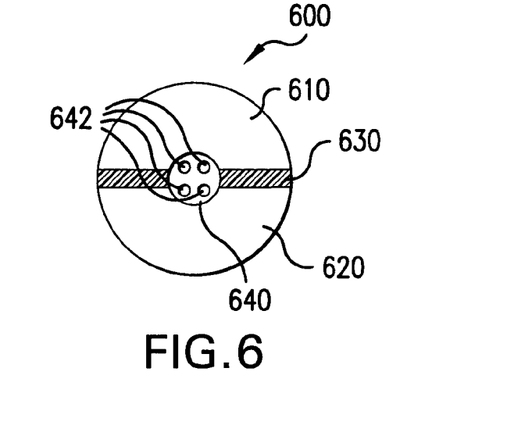
FIG. 6 is a front-end view of an alternative distal end configuration of a catheter with sensing electrodes, in accordance with yet another embodiment of the present invention.

FIG. 6 is a front-end view of an alternative distal end configuration of a catheter with sensing electrodes, in accordance with yet another embodiment of the present invention. In FIG. 6, a sensor 600 may include a first electrode 610 and a second electrode 620 separated and possibly fixed together by an insulator 630 to form a generally circular shape. In addition, an opening 640 may be located substantially axially aligned with a center of sensor 600, may be of a generally circular shape and may be substantially filled with insulator 630 in which one or more openings 642 may be placed to permit one or more needles (not shown) to be introduced through one or more openings 642. Insulator 630 may not only insulate any needles that may pass through one or more openings 642, but also may provide one or more guides and added stability for the needles. For example, in the embodiment of the present invention shown in FIG. 6, sensor 600 may accommodate up to four needles. However, other embodiments are contemplated in which less than four as well as more than four openings may be disposed in the sensor.

Similar to FIG. 5, in FIG. 6, although not shown, sensor 600 may also have generally perpendicular and proximally extending walls similar to walls 114, 124 in FIG. 2 and walls 314, 324 in FIG. 4 to fit into or over the distal end of a catheter. Alternative shapes are contemplated including, for example, oval and/or square.

Figure 7:
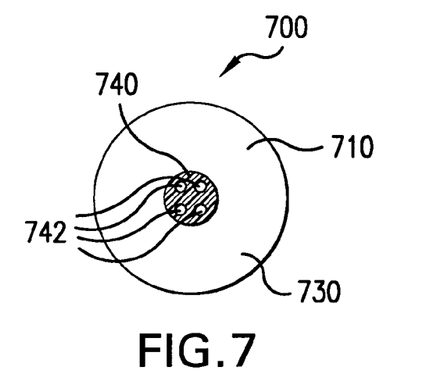
FIG. 7 is a front-end view of an alternative distal end configuration of a catheter with sensing electrodes, in accordance with yet another embodiment of the present invention.

FIG. 7 is a front-end view of an alternative distal end configuration of a catheter with sensing electrodes, in accordance with yet another embodiment of the present invention. In FIG. 7, a sensor 700 may include a single electrode 710, with an insulator 730 disposed in an opening 740 in single electrode 710. Single electrode 710 may be in a generally circular shape, and opening 740 also may be of a generally circular shape and may be located substantially axially aligned with a center of single electrode 710. In addition, insulator 730 may include one or more openings 742 to permit one or more needles (not shown) to be introduced through one or more openings 742. Insulator 730 may not only insulate any needles that may pass through the one or more openings 742, but may also provide one or more guides and added stability for the needles. For example, in the embodiment of the present invention shown in FIG. 7, sensor 700 may accommodate up to four needles and/or micro-needles. However, alternative embodiments are contemplated in which less than four as well as more than four openings may be disposed in sensor.

Similar to FIGS. 5 and 6, in FIG. 7, although not shown, sensor 700 may also have one or more generally perpendicular and proximally extending walls similar to walls 114, 124 in FIG. 2 and walls 314, 324 in FIG. 4 to fit into or over the distal end of a catheter. Alternative shapes are contemplated including, for example, oval and/or square.

Figure 8:
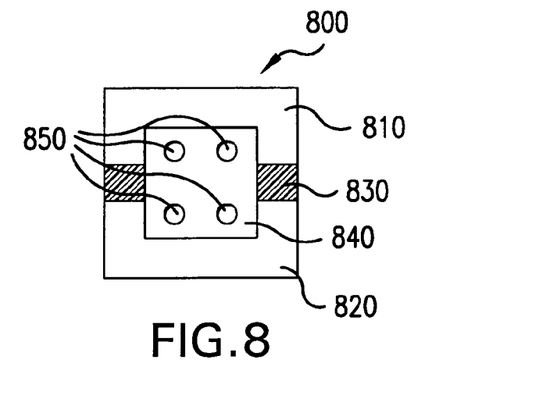
FIG. 8 is a front-end view of an alternative distal end configuration of a catheter with sensing electrodes, in accordance with yet another embodiment of the present invention.

FIG. 8 is a front-end view of an alternative distal end configuration of a catheter with sensing electrodes, in accordance with yet another embodiment of the present invention. In FIG. 8, a sensor 800 may include a first electrode 810 and a second electrode 820 fixed together by an insulator 830 to form a generally square shape. In addition, an opening 840 in sensor 800 may be of a generally square shape to permit one or more needles to be introduced through opening 840. For example, in the embodiment of the present invention shown in FIG. 8, four needles 850 are shown. However, alternative embodiments are contemplated in which less than four as well as more than four needles may be used. In another embodiment of the present invention, sensor 800 may include a substantially square shape with rounded corners and/or edges to permit easier movement into and out of a patient's body.

Similar to FIGS. 5 through 7, in FIG. 8, although not shown, sensor 800 may also have generally perpendicular and proximally extending walls similar to walls 114, 124 in FIG. 2 and walls 314, 324 in FIG. 4 to fit into or over the distal end of a catheter. Alternative shapes are contemplated including, for example, oval and/or square.

Figure 9:
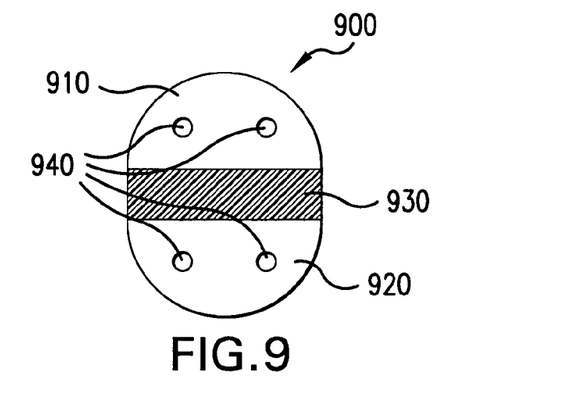
FIG. 9 is a front-end view of an alternative distal end configuration of a catheter with sensing electrodes, in accordance with yet another embodiment of the present invention.

FIG. 9 is a front-end view of an alternative distal end configuration of a catheter with sensing electrodes, in accordance with another embodiment of the present invention. In FIG. 9, a sensor 900 may include a first electrode 910 and a second electrode 920 separated and possibly fixed together by an insulator 930 running therebetween to form a substantially oval shape. In addition, one or more openings 940 may be located in first electrode 910 and/or second electrode 920 to permit one or more needles to be introduced through one or more openings 940. In this embodiment, insulator 930 may insulate only first electrode 910 and second electrode 920 from each other. Any needles that pass through the one or more openings 940 may be non-conductive or, alternatively, may be further insulated from first and/or second electrodes 910, 920 by an insulating coating that may be applied to the interior walls defining each of one or more openings 940 or to the needles. One or more openings 940 may also provide added stability for any needles that may pass through the one or more openings 940. For example, in the embodiment of the present invention shown in FIG. 9, sensor 900 may accommodate up to four needles. However, other embodiments are contemplated in which less than four as well as more than four openings may be disposed in the sensor. In other embodiments of the present invention, one or more openings 940 may be disposed in insulator 930 and/or any combination of one or more openings 940 in electrodes 910, 920 and insulator 930.

Similar to FIGS. 5 through 8, in FIG. 9, although not shown, sensor 900 may also have generally perpendicular and proximally extending walls similar to walls 114, 124 in FIG. 2 and walls 314, 324 in FIG. 4 to fit into or over the distal end of a catheter. Alternative shapes are contemplated including, for example, oval and/or square.

Figure 10:
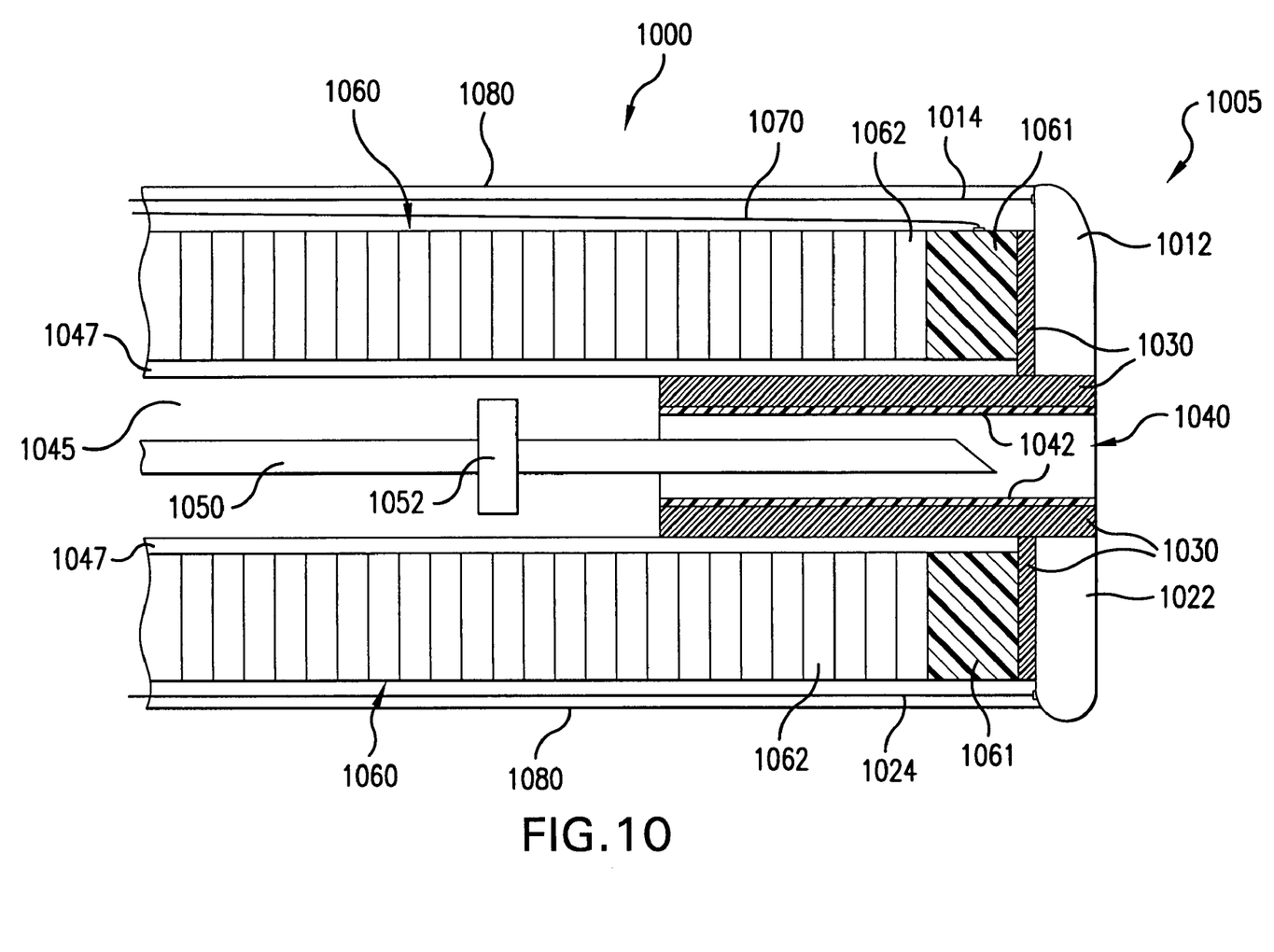
FIG. 10 is a cross-sectional side view of a distal end of a deflectable tip catheter with sensing electrodes, in accordance with an embodiment of the present invention.

FIG. 10 is a cross-sectional side view of a distal end of a deflectable tip catheter with sensing electrodes, in accordance with an embodiment of the present invention. In FIG. 10, a distal end of a deflectable tip catheter 1000 may include a sensor 1005 having a first electrode 1012 and to a second electrode 1022. Sensor 1005 may be a substantially circular disk without any proximally extending walls as in sensors 100 and 300 of FIG. 1 and FIG. 3, respectively. First electrode 1012 may be coupled to a first lead wire 1014, which may run from a proximal end to a distal end of deflectable tip catheter 1000, and second electrode 1022 may be coupled to a second lead wire 1024, which also may run from the proximal end to the distal end of deflectable tip catheter 1000. First electrode 1012 and second electrode 1022 may be separated, and possibly fixed to each other, by an insulator 1030. Consequently, first electrode 1012 and second electrode 1022 may be electrically insulated from each other. For example, sensor 1005 may be similar to sensor 600 from FIG. 6, except that in the present embodiment in FIG. 10, sensor 1005 is illustrated as having a single opening 1040 with a single needle 1050. Sensor 1005 also may be of any other suitable configuration, such as one of the configurations described or discussed above in relation to FIGS. 1 through 9. A proximal surface of sensor 1005 may be fixed at the distal end of deflectable tip catheter 1000, for example, by using insulator 1030, which may be seen to extend substantially perpendicularly and proximally from the distal surface of sensor 1005 through opening 1040 and into a lumen 1045 that runs from the proximal end to the distal end of catheter 1000. Lumen 1045 may be defined by an interior surface of an inner catheter wall 1047, which may also run from the proximal end to the distal end of catheter 1000. In addition, sensor 1005 may be fixed at the distal end of catheter 1000 by another portion of insulator 1030, which may be disposed proximal to the proximal surface of sensor 1005. Although first electrode 1012 and second electrode 1022 may be seen to have different configurations in FIG. 10, their shapes are merely illustrative of some of the possible electrode configurations of sensor 1005. The specific size and shape of first electrode 1012 and second electrode 1022 may be varied.

In FIG. 10, opening 1040 may include an interior lining 1042 fixed to the interior surface of the substantially proximally extending portion of insulator 1030. Interior lining 1042 may be a heat shrink material that may coat/adhere to the interior wall of the substantially proximally extending portion of insulator 1030 to provide additional insulation and an improved sliding surface for needle 1050. As seen in FIG. 10, needle 1050 may extend from the proximal end to the distal end of catheter 1000 and have a send marker band 1052 encircling a portion of needle 1050 near a distal end of needle 1050. Send marker band 1052 may have a substantially annular shape with a size corresponding to that of opening 1040. As a result, when needle 1050 is extended into and out of opening 1040, send marker band 1052 may slide into and out of opening 1040 to guide needle 1050 through and to provide support for needle 1050 in opening 1040. Send marker band 1052 may include a non-conducting material to insulate needle 1050 from sensor 1005. Send marker band 1052 may also act as a depth send for needle 1050 to prevent needle 1050 from extending too far into the target tissue. For example, if the distal side of sensor 1005 is in contact with the target tissue, the extension of needle 1050 may be limited by send marker band 1052 when it contacts the target tissue at the distal side of opening 1040.

In FIG. 10, in accordance with an embodiment of the present invention, catheter 1000 may include a deflection coil 1060 that may be fixed to the exterior side of inner catheter wall 1047 to enable the distal end of catheter 1000 to be selectively deflected. At least one pull/push wire 1070 may be attached to an exterior surface of deflection coil 1060 near sensor 1005 to enable the selective deflection of the distal end of catheter 1000. Deflection coil 1060 may be annular in shape including a solid cell ring 1061 located at the distal end of deflection coil 1060 and multiple compressive cells 1062 located proximal to solid cell ring 1061. The multiple compressive cells 1062 may be in a non-compressed state at rest and may compress and/or expand in response to the pulling or pushing of at least one pull/push wire 1070, which may be attached to solid cell ring 1061. Solid cell ring 1061, generally, may be made of a non-compressive material to provide a strong and stable anchoring point for at least one pull/push wire 1070. Each of the multiple compressive cells 1062 may include a material that may have a memory to help return the compressive cell back to its uncompressed state when deflection coil 1060 is un-deflected. For example, in an embodiment of the present invention, distal ends of four pull/push wires 1070 may be equidistantly fixed to and around the exterior surface of deflection coil 1060 on solid cell ring 1061 to provide four-way directional control of the distal end of catheter 1000. An exterior casing 1080 may run from the proximal end to the distal end of catheter 1000 and be fixed to an outer edge of the proximal side of sensor 1005 to enclose but not bind lead wires 1014, 1024 and one or more pull/push wires 1070. Use of deflection coil 1060 to control the position of the distal end of catheter 1000 enables sensor 1005 to be more easily positioned directly over and against the target tissue site that is to be treated.

In the embodiment in FIG. 10, the four pull/push wires 1070 may be separated by approximately 90° to permit a single pull/push wire 1070 to control movement in a single direction, for example, 0°, 90°, 180° and 270°; or up, right, down and left; or north, east, south and west; or 12, 3, 6 and 9 o'clock. Also, in this embodiment, simultaneously pulling or pushing on two adjacent pull/push wires 1070 may control the movement of the distal end of catheter 1000 in two directions to move the distal end of catheter 1000 between two adjacent pull/push wires 1070; for example, pulling equally, on both the north and west pull/push wires 1070 may result in movement in the northwest direction (that is, half-way between 10 and 11 o'clock). Similarly, pulling twice as hard on the north wire as on the west wire may result in movement in the north, northwest direction (that is, 11 o'clock). Of course, it is to be understood that the above directions are relative to the position of the distal end of catheter 1000, which may have changed from its original position before being inserted into a lumen in a patient.

Alternatively, in FIG. 10, deflection coil 1060 may include two 180° arcs that may be disposed under first electrode 1012 and second electrode 1022. Accordingly, one or more pull/push wires 1070 may be attached to each arc of the deflection coil 1060 to permit the separate control of each deflection coil arc, as described above. Similarly, deflection coil 1060 may include multiple arcs with one or more pull/push wires 1070 disposed under the electrodes and around the exterior of inner catheter wall 1047. In embodiments with sensor 1005 having more than two electrodes, separate arcs may be disposed under each electrode to permit the selective deflection of sensor 1005.

Figure 11:
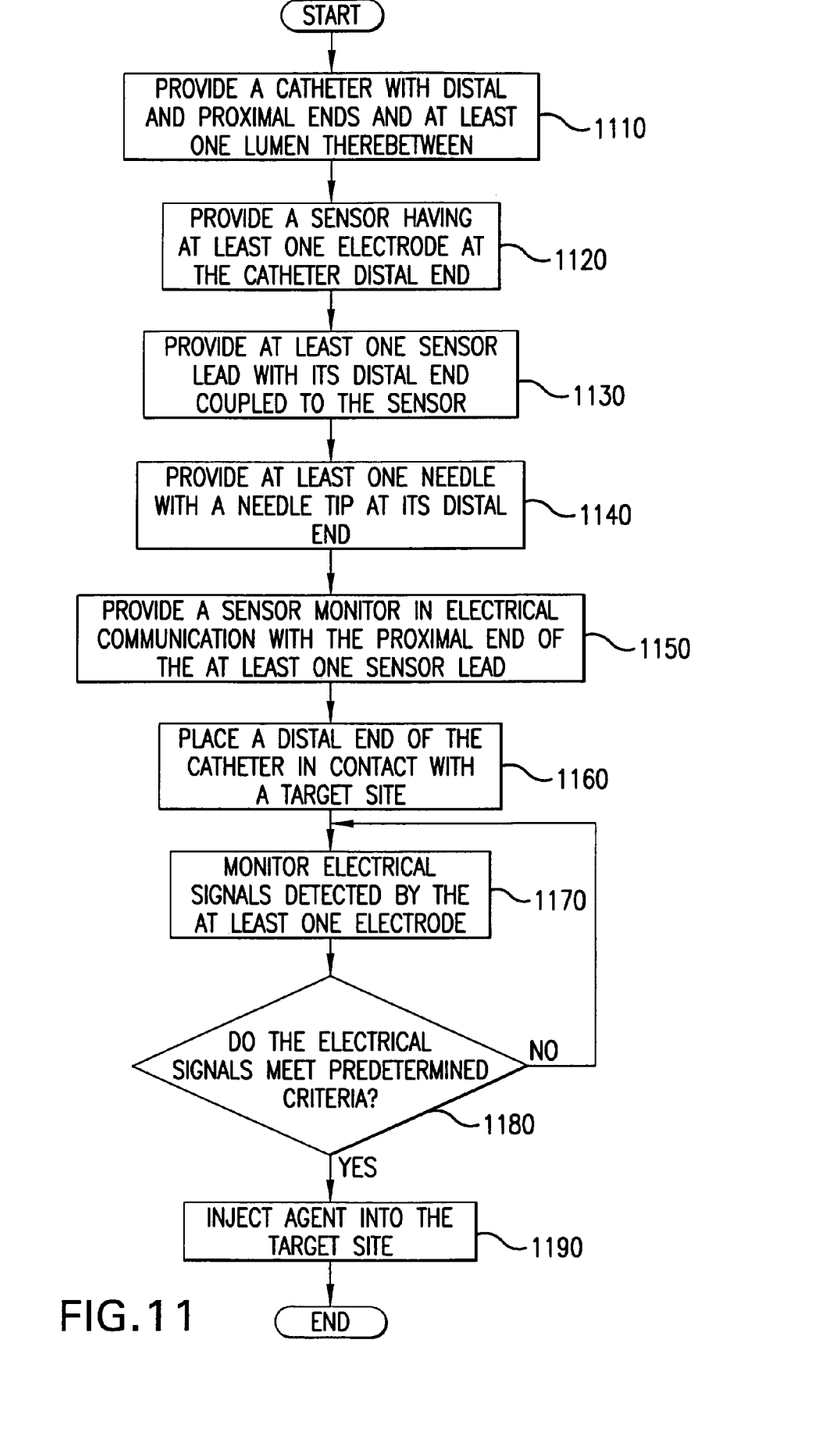
FIG. 11 is a flow diagram of a method for performing a sensor-guided catheter-based injection, in accordance with an embodiment of the present invention.

FIG. 11 is a flow diagram of a method for performing a sensor-guided catheter-based injection, in accordance with an embodiment of the present invention. In FIG. 11, the method may include providing (1110) a catheter with a distal end and a proximal end and at least one lumen extending therebetween. The method also may include providing (1120) a sensor located at the catheter distal end, the sensor including at least one electrode, the electrode being located at the catheter distal end such that the electrode may contact a target site when the catheter distal end is placed at the target site. The sensor may also include at least two electrodes and an insulator to electrically insulate the at least two electrodes from one another. The method may include providing (1130) at least one sensor lead, a distal end of each at least one sensor lead may be in electrical communication with a corresponding sensor, and a proximal end of each at least one sensor lead may extend to the catheter proximal end. The method may further include providing (1140) at least one needle having a distal end in the form of a needle tip and a proximal end adapted to receive a fluid injection, the at least one needle may be slidably disposed in one of the at least one catheter lumens between a retracted position in which the needle tip is within the catheter distal end and an extended position in which the needle tip is extended beyond the catheter distal end, the at least one needle may be electrically insulated from the at least one electrode. The method may also include providing (1150) a sensor monitor in electrical communication with the proximal end(s) of the at least one sensor lead to monitor electrical signals from the at least one electrode. The method may further include placing (1160) a distal end of the catheter in contact with a target site within a patient's body. The method may include monitoring (1170) electrical signals detected by the electrode(s) and determining (1180) whether the electrical signals detected by the electrode(s) meet a predetermined injection criteria. The method may continue monitoring (1170) the electrical signals, if the electrical signals do not meet the predetermined injection criteria. The method may include injecting (1190) an agent, for example, a therapeutic agent, into the target site and the method may end, if the electrical signals detected by the electrode(s) meet the predetermined injection criteria.

Figure 12:
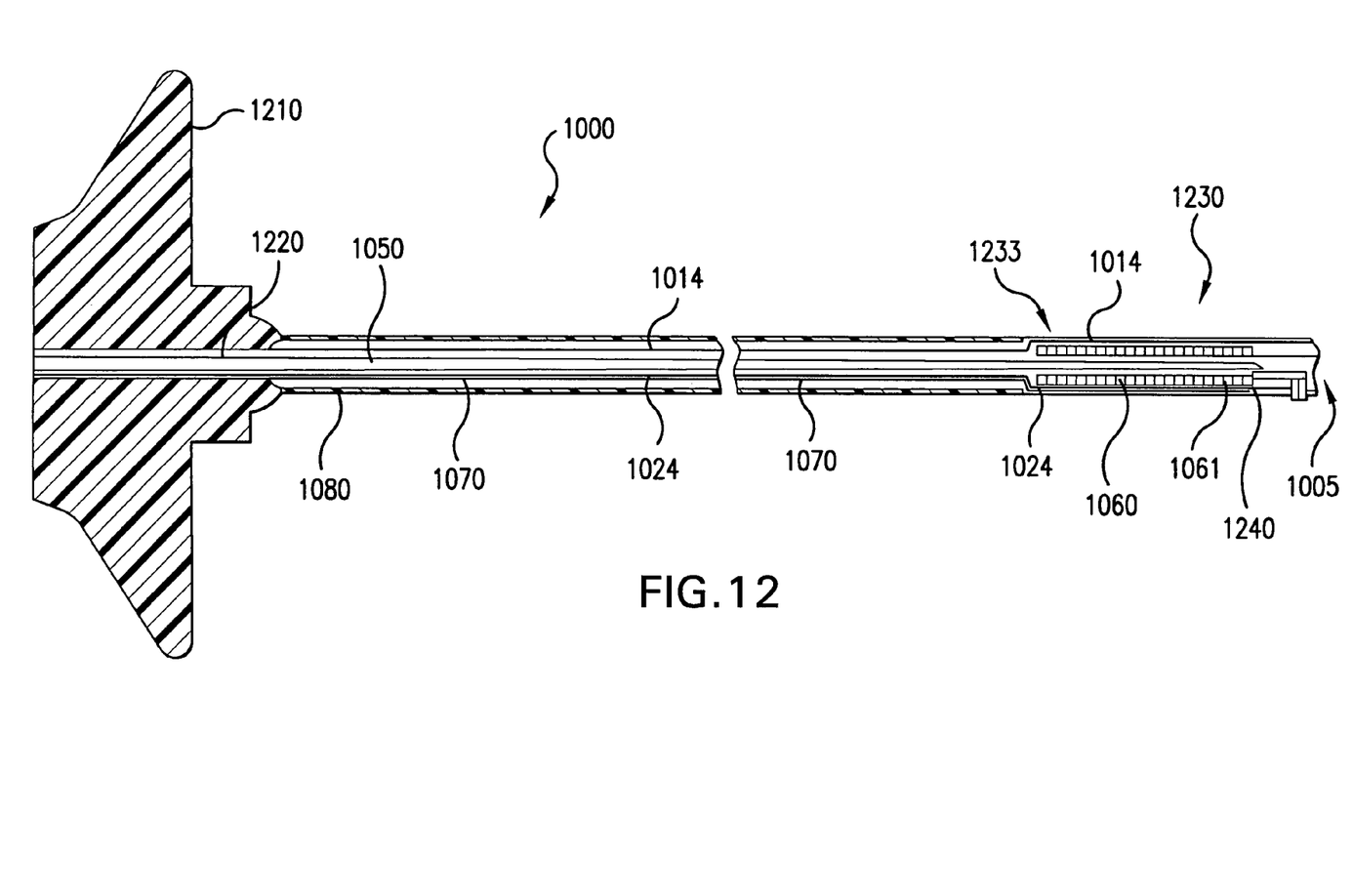
FIG. 12 is a cross-sectional side view of a deflectable tip catheter, in accordance with an embodiment of the present invention

FIG. 12 is a cross-sectional side view of a deflectable tip catheter, in accordance with an embodiment of the present invention. In FIG. 12, catheter 1000 may include a push/pull deflectable tip actuator 1210 with a lumen 1220 extending from a proximal end to a distal end of push/pull deflectable tip actuator 1210. A distal end of lumen 1220 may be co-axially aligned with a proximal end of lumen 1045 of catheter 1000 to form a continuous lumen from a proximal end of lumen 1220 to the distal end of lumen 1045. Push/pull deflectable tip actuator 1210 may be attached to the proximal end of catheter 1000 using, for example, an adhesive. Push/pull deflectable tip actuator 1210 may also be attached to the proximal end of push/pull wire 1070, and a distal end of push/pull wire 1070 may be attached near the distal end of catheter 1000 at a distal end of a deflectable tip 1230 of catheter 1000. Deflectable tip 1230 may be deflected in a predetermined direction, as a result of where push/pull wire 1070 may be attached at, for example, a solder joint 1240, to solid cell ring 1061 in deflectable tip 1230, by manually pushing/pulling a distal side of push/pull deflectable tip actuator 1210. The amount of deflection may be controlled by the amount of force exerted against push/pull deflectable tip actuator 1210. Deflectable tip 1230 may deflect from its proximal end 1233. In general, the pushing/pulling may be applied by a surgeon's hands and/or fingers. In other embodiments of the present invention, two or more push/pull wires 1070 may be attached at their respective proximal ends to push/pull deflectable tip actuator 1210 and at their distal ends to the deflectable tip 1230.

As illustrated in FIG. 12, distal ends of first lead wire 1014 and second lead wire 1024 may be attached to a proximal end of sensor 1005 and may extend proximally away from sensor 1005 and through lumen 1220 of push/pull deflectable tip actuator 1210.

A more detailed description of the operation of a deflectable tip catheter and a control assembly may be found in U.S. Pat. No. 6,083,222, issued on Jul. 4, 2000 and entitled "Deflectable Catheter for Ablating Cardiac Tissue," which is hereby incorporated by reference in its entirety.

Figure 13:
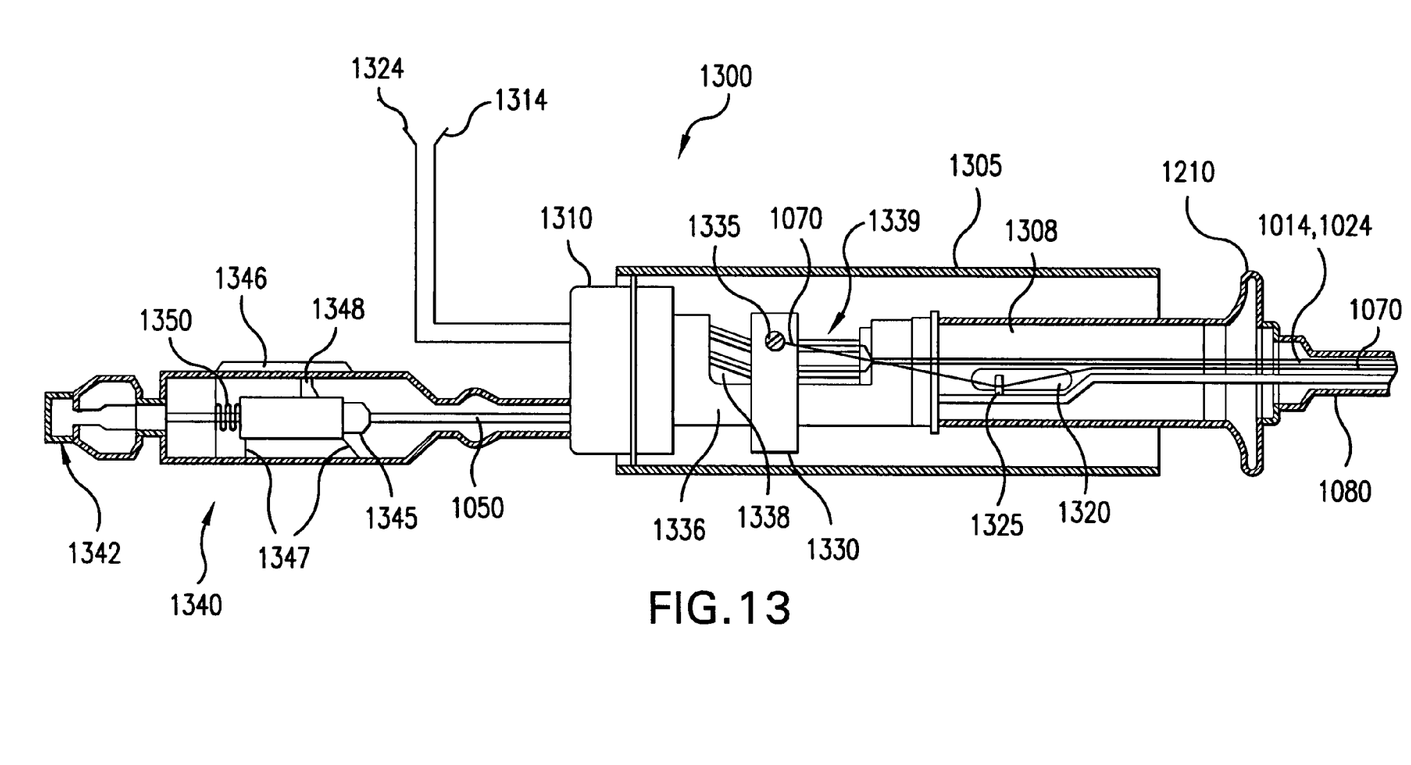
FIG. 13 is a cross-sectional, cut-away side view of the proximal end of the deflectable tip catheter of FIG. 12 with attached control mechanisms for elements in the deflectable tip catheter, in accordance with an embodiment of the present invention.

FIG. 13 is a cross-sectional, cut-away side view of the proximal end of the deflectable tip catheter of FIG. 12 with attached control mechanisms for elements in the deflectable tip catheter, in accordance with an embodiment of the present invention. In FIG. 13, control assembly may include a manifold 1305 having a proximal end and a distal end. The distal end of a manifold 1305 may be attached to the proximal end of push/pull deflectable tip actuator 1210 and first lead wire 1014 and second lead wire 1024 may be seen to extend through a coaxial lumen 1308 of the control assembly 1300 and out of a manifold cap 1310 in a proximal end of manifold 1305. The proximal ends of first lead wire 1014 and second lead wire 1024 may be connected to electrical signal monitoring equipment to display any electrical signals measured by sensor 1005.

In FIG. 13, in accordance with an embodiment of the present invention, control assembly 1300 may be fixedly and/or removably attached to push/pull deflectable tip actuator 1210. Push/pull wire(s) 1070 may extend proximally from deflectable tip 1230 of catheter 1000 through lumen 1308 around a tension bar 1320 with a tension post 1325 and terminate by attaching to a push/pull wire anchor 1330 in control assembly 1300. Specifically, the proximal ends of push/pull wire(s) 1070 may be anchored by, for example, a screw 1335, to push/pull wire anchor 1330. Push/pull wire anchor 1330 may be proximally biased to place push/pull wire(s) 1070 under tension between push/pull wire anchor 1330 and push/pull actuator 1210. Push/pull wire(s) 1070 may be used to control the amount of deflection of deflectable tip 1230 of catheter 1000 by activating push/pull actuator 1210. Push/pull wire anchor 1330 may be slidably engaged to a slide assembly 1336, which may be rigidly attached to an interior distal side of manifold cap 1310 at the proximal end of control assembly 1300. Slide assembly 1336 may include a lumen 1338 extending from its proximal end to its distal end through which sensor leads 1314, 1324 and needle 1050 may pass. Lumen 1338 may be axially aligned with and in communication with lumen 1308 of control assembly 1300. Lumen 1338 may also be accessible through an opening 1339 in slide assembly 1336.

In accordance with an embodiment of the present invention, in FIG. 13, needle 1050 may extend through lumens 1308, 1338 and out manifold cap 1310 of control assembly 1300, and into a distal end of an injection actuator 1340. Specifically, needle 1050 may extend from a hub 1342, for example, but not limited to, a Luer hub, at a proximal end of injection actuator 1340, pass through a firing mechanism 1345 and pass out of a distal end of injection actuator 1340 and into manifold cap 1310 at the proximal end of control assembly 1300. A proximal end of hub 1342 may receive the therapeutic agent and may be in fluid communication with the needle 1050. A push button actuator 1346 may be attached to and through an exterior surface of injection actuator 1340 to control firing mechanism 1345, which in turn may control the extension of the distal end of needle 1050 for the delivery of the therapeutic agent to the target tissue.

In FIG. 13, in accordance with an embodiment of the present invention, firing mechanism 1345 may be axially aligned with and attached around needle 1050, and slidably disposed in injection actuator 1340. Specifically, firing mechanism 1345 may be slidably attached to a rail 1347 that may be rigidly attached to an interior wall of injection actuator 1340. Firing mechanism 1345 may move proximally and distally along rail 1347 to retract and extend, respectively, needle 1050 out of the distal end of catheter 1000. Firing mechanism 1345 may be biased toward the distal end of injection actuator 1340 by a spring 1350, which may be disposed between a proximal end of firing mechanism 1345 and an interior distal side of a proximal end of injection actuator 1340. Firing mechanism 1345 may include a plunger 1348 that may be disposed in firing mechanism 1345 and may extend away from firing mechanism 1345 in a plane axially aligned with and substantially perpendicular to a central axis of firing mechanism 1345. When firing mechanism 1345 is moved proximally, plunger 1348 may extend away from firing mechanism 1345 and releasably engage an opening in push button actuator 1346 to hold piston 1345 in a locked, ready to be fired, position within firing mechanism body 1347. Plunger 1348 may be biased, for example, by a spring mechanism, to extend perpendicularly out and away from the central axis of plunger 1348 to engage the opening in push button actuator 1346 when plunger 1348 has moved to a predetermined position within injection actuator 1340.

In FIG. 13, in accordance with an embodiment of the present invention, push button actuator 1346 may be used to fire needle 1050 by pushing down on plunger 1348, which may release plunger 1348 from the opening in push button actuator 1346. For example, push button actuator 1346 may be hinged at a distal end to injection actuator 1340 so that when push button actuator 1346 is pressed, the proximal end of push button actuator 1346 moves inwardly toward the proximal end of firing mechanism 1345 to permit plunger 1348 to slide out of the opening in push button actuator 1346. Pushing plunger 1348 back through the opening in push button actuator 1346 may release firing mechanism 1345 to be moved distally by spring 1350. Consequently, the distal end of needle 1050 may extend past the distal end of catheter and into the target tissue that sensor 1005 may be in contact with. Hub 1342 may move distally with firing mechanism 1345 and hub 1342 may be manually pulled away from the proximal end of injection actuator 1340 to re-lock firing mechanism 1345 in push button actuator 1346 with plunger 1348.

In FIG. 13, in accordance with an embodiment of the present invention, although not its main function, hub 1342 may limit the firing distance of spring 1350 when a distal end of hub 1342 strikes the proximal end of injection actuator 1340. Hub 1342, in general, is at a predetermined fixed distance from the proximal end of injection actuator 1340 and thus may not contact the proximal end of injection actuator 1340 if, for example, the injection depth controlled by send marker band 1052 on needle 1050 is less than the predetermined fixed distance hub 1342 is from the proximal end of injection actuator 1340.

A detailed description of embodiments of catheter assemblies that may be used in embodiments of the present invention may be found in co-pending U.S. patent application Ser. No. 09/635,083, filed by the same assignee on Aug. 8, 2000 and entitled "Catheter Shaft Assembly," which is hereby incorporated by reference in its entirety.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene;

anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1") and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homdimers, heterodimers, or combinations thereof, alone or together with other molecules. Alternatively, or in addition, molecules capable of inducing an upstream or downstream effect of a BMP can be provided. Such molecules include any of the "hedghog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

Any of the therapeutic agents may be combined to the extent such combination is biologically compatible.

Any of the above mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

In a preferred embodiment, the polymer is polyacrylic acid available as HYDROPLUS® (Boston Scientific Corporation, Natick, Mass.), and described in U.S. Pat. No. 5,091,205, the disclosure of which is incorporated by reference herein. In a more preferred embodiment, the polymer is a co-polymer of polylactic acid and polycaprolactone.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

Although the present invention has been disclosed in detail, it should be understood that various changes, substitutions, and alterations may be made herein, the present invention is intended to cover various modifications and equivalent arrangements. Other examples are readily ascertainable from the above description by one skilled in the art and may be made without departing from the spirit and scope of the present invention as defined by the following claims.

What is claimed is:

1. A medical device, comprising:
    a catheter with a distal end and a proximal end and at least one catheter lumen extending therebetween;
    a sensor located at the catheter distal end; and
    at least two sensor leads, a distal end of each of the sensor leads in electrical communication with the sensor, and a proximal end of each of the sensor leads extending to the catheter proximal end;
        wherein the sensor includes at least two electrodes, where each electrode is in electrical communication with at least one of the at least two sensor leads, and the electrodes are located at the catheter distal end such that the electrodes contact a target site when the catheter distal end is placed at the target site;
        wherein each electrode has an end plate with a major axis that is substantially perpendicular to a longitudinal axis of the catheter, and wherein at least a portion of the end plate overhangs the distal end of the catheter.

2. The medical device of claim 1, wherein the catheter proximal end is adapted to receive a therapeutic agent and the catheter distal end is adapted to eject the therapeutic agent.

3. The medical device of claim 1, wherein the sensor further comprises:
    an insulator to electrically insulate the at least two electrodes from one another.

4. The medical device of claim 3, further comprising:
    a needle having a distal end in the form of a needle tip and a proximal end to receive a fluid injection, the needle slidably disposed in one of the at least one catheter lumens between a retracted position in which the needle tip is within the catheter distal end and an extended position in which the needle tip extends beyond the catheter distal end, wherein the needle is electrically insulated from the at least two electrodes.

5. The medical device of claim 4, wherein the needle comprises: a solid therapeutic agent.

6. The medical device of claim 5, wherein the needle is to break off a predetermined length of the solid therapeutic agent when the needle tip extends beyond the catheter distal end and into the target site.

7. The medical device of claim 5, wherein the solid therapeutic agent comprises: a polymer and cells.

8. The medical device of claim 3, further comprising:
    a plurality of needles, each needle slidably disposed in a corresponding one of a plurality of catheter lumens, each needle having a distal end with a needle tip and a proximal end to receive a fluid injection, wherein
    each needle is slidably displaceable between a retracted position in which the needle tip is within the catheter and an extended position in which the needle tip extends beyond the catheter distal end, and
    each needle is electrically insulated from the at least two electrodes.

9. The medical device of claim 8, wherein each of the at least two electrodes has at least one opening in a face that contacts the target site, and at least one of the plurality of needles passes through one of the electrode face openings when the needle is in the extended position.

10. The medical device of claim 9, wherein each needle is insulated from electrical contact with the electrode through which the needle passes.

11. The medical device of claim 3, further comprising:
    a needle slidably disposed in one of the at least one catheter lumens, the needle having a distal end with an array of micro-needles with needle tips and a proximal end to receive a fluid injection, wherein
    the needle is slidably displaceable between a retracted position in which the needle tips are within the catheter and an extended position in which the needle tips extend beyond the catheter distal end, and
    the needle is electrically insulated from the at least two electrodes.

12. The medical device of claim 11, wherein, when in the extended position, the array of micro-needles passes between the at least two electrodes through an opening in the insulator.

13. The medical device of claim 1, wherein the sensor has a substantially circular surface to contact the target site.

14. The medical device of claim 1, wherein the sensor has a substantially oval surface to contact the target site.

15. The medical device of claim 1, wherein the sensor has a substantially rectangular surface to contact the target site.

16. The medical device of claim 1, wherein the sensor further comprises an adhesive surface.

17. The medical device of claim 1, wherein the sensor further comprises a plurality of protrusions.

18. The medical device of claim 1, wherein the end plate further comprises an outer circular edge.

19. A sensor-equipped catheter injection system, comprising:
a catheter with a distal end and a proximal end and at least one lumen extending therebetween;
a sensor located at the catheter distal end, the sensor including at least two electrodes, the electrodes being located at the catheter distal end such that the electrodes contact a target site when the catheter distal end is placed at the target site, and the sensor further includes an insulator to electrically insulate the at least two electrodes from one another;
at least two sensor leads, a distal end of each of the sensor leads in electrical communication with one of said at least two electrodes, and a proximal end of each of the sensor leads extending to the catheter proximal end;
at least one needle having a distal end in the form of a needle tip and a proximal end to receive a therapeutic agent, slidably disposed in one of the at least one catheter lumens between a retracted position in which the needle tip is within the catheter distal end and an extended position in which the needle tip extends beyond the catheter distal end, the at least one needle being electrically insulated from the at least two electrodes; and
a sensor monitor in electrical communication with the proximal ends of the at least two sensor leads to monitor electrical signals from the at least two electrodes;
wherein each electrode has an end plate with an outer circular edge and a major axis that is substantially perpendicular to a longitudinal axis of the catheter, and wherein at least a portion of the end plate overhangs the distal end of the catheter.

20. The sensor-equipped catheter injection system of claim 19, wherein, when in the extended position, the needle passes between the at least two electrodes through an opening in the insulator.

21. The sensor-equipped catheter injection system of claim 19, wherein said at least one needle comprises:
a plurality of the plurality of needles, each needle slidably disposed in a corresponding one of a plurality of catheter lumens, each needle having a distal end with a needle tip and a proximal end to receive a therapeutic agent, wherein each needle is slidably displaceable between a retracted position in which the needle tip is within the catheter and an extended position in which the needle tip extends beyond the catheter distal end, and each of the needles is electrically insulated from the at least two electrodes.

22. The sensor-equipped catheter injection system of claim 21, wherein at least one of the at least two electrodes has at least one opening in a face that contacts the target site, and at least one of the plurality of needles passes through the electrode face opening when in the extended position.

23. The sensor-equipped catheter injection system of claim 19, wherein the needle distal end has an array of micro-needles, the needle is slidably displaceable between a retracted position in which the array of micro-needles is within the catheter and an extended position in which the array of micro-needles extends beyond the catheter distal end, and the needle is electrically insulated from the at least two electrodes.

24. The sensor-equipped catheter injection system of claim 23, wherein, when in the extended position, the array of micro-needles passes between the at least two electrodes through an opening in the insulator.

25. The sensor-equipped catheter injection system of claim 19, further comprising:
an injection actuator located at the proximal end of the catheter to cause the distal end of the at least one needle to extend the needle tip beyond the distal end of the catheter.

26. The sensor-equipped catheter injection system of claim 25, wherein the injection actuator comprises:
a firing mechanism attached to the at least one needle and slidably attached with respect to the injection actuator and biased toward the distal end of the catheter by a spring when the firing mechanism is in a locked, ready to fire position.

27. The sensor-equipped catheter injection system of claim 26, wherein the injection actuator further comprises:
a hub attached at the proximal end of the at least one needle and slidably connected at a proximal end of the injection actuator.

28. The sensor-equipped catheter injection system of claim 27, wherein the hub is biased toward the distal end of the catheter by the spring when the firing mechanism is in a locked, ready to fire position.

29. The sensor-equipped catheter injection system of claim 27, wherein the hub is adapted to be manually displaced in the proximal direction to place the firing mechanism in the locked, ready to fire position.

30. The sensor-equipped catheter injection system of claim 29, wherein the firing mechanism comprises:
a plunger to lock the firing mechanism in the ready to fire position by extending away from the firing mechanism to engage an opening in a push button actuator.

31. The sensor-equipped catheter injection system of claim 30, wherein the plunger is biased away from the firing mechanism.

32. The sensor-equipped catheter injection system of claim 19, wherein the sensor further comprises an adhesive surface.

33. The sensor-equipped catheter injection system of claim 19, wherein the sensor further comprises a plurality of protrusions.

34. A method for sensor-guided catheter-based injection, comprising:
providing a catheter with a distal end and a proximal end and at least one lumen extending therebetween;
providing a sensor located at the catheter distal end, the sensor including at least two electrodes, the electrodes being located at the catheter distal end such that the electrodes contact a target site when the catheter distal end is placed at the target site, and the sensor further including an insulator to electrically insulate the at least two electrodes from one another, wherein the sensor comprises a rough surface and an end plate, at least a portion of the end plate overhanging the distal end of the catheter;
providing at least two sensor leads, a distal end of each of the sensor leads being in electrical communication with the sensor, and a proximal end of each of the sensor leads extending to the catheter proximal end;
providing at least one needle having a distal end in the form of a needle tip and a proximal end adapted to receive a therapeutic agent, the at least one needle being slidably disposed in one of the at least one catheter lumens between a retracted position in which the needle tip is within the catheter distal end and an extended position in which the needle tip extends beyond the catheter distal end, the at least one needle being electrically insulated from the at least two electrodes;

providing a sensor monitor in electrical communication with the proximal ends of the at least two sensor leads to monitor electrical signals from the at least two electrodes;

placing a distal end of the catheter in contact with a target site within a patient's body;

securing the sensor to a tissue surface at the target site by the rough surface of the sensor;

monitoring electrical signals detected by the electrodes;

determining whether the electrical signals detected by the electrodes meet a predetermined injection criteria; and injecting the therapeutic agent into the target site, if the electrical signals detected by the electrodes meet the predetermined injection criteria.

35. The method of claim 34, wherein the target site is an AV node of the heart; and the monitor is an EKG monitor.

36. The method of claim 35, wherein the predetermined injection criteria is abnormal electrical activity signifying one of bradyarrhythmia and ventricular tachyarrhythmia.

37. The method of claim 36, wherein the therapeutic agent is a gene therapy agent.

38. The method of claim 34, further comprising:

providing an injection actuator connected to the proximal end of the catheter, the injection actuator to control when the needle tip is extended and retracted by releasing and locking into place a distally biased firing mechanism that is attached at approximately the proximal end of the needle.

39. The method of claim 34, wherein the sensor further comprises an adhesive surface.

40. The method of claim 34, wherein the sensor further comprises a plurality of protrusions.

* * * * *